(12) United States Patent
Sano

(10) Patent No.: US 11,944,482 B2
(45) Date of Patent: Apr. 2, 2024

(54) IMAGING CONTROL DEVICE, RADIOGRAPHY SYSTEM, IMAGING CONTROL METHOD, AND IMAGING CONTROL PROGRAM

(71) Applicant: FUJIFILM CORPORATION, Tokyo (JP)

(72) Inventor: Menamu Sano, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 279 days.

(21) Appl. No.: 17/577,336

(22) Filed: Jan. 17, 2022

(65) Prior Publication Data

US 2022/0257210 A1 Aug. 18, 2022

(30) Foreign Application Priority Data

Feb. 18, 2021 (JP) .................. 2021-024604

(51) Int. Cl.
*A61B 6/00* (2006.01)
*A61B 6/02* (2006.01)
*A61B 6/40* (2024.01)
*A61B 6/50* (2024.01)

(52) U.S. Cl.
CPC ................ *A61B 6/54* (2013.01); *A61B 6/025* (2013.01); *A61B 6/4035* (2013.01); *A61B 6/502* (2013.01)

(58) Field of Classification Search
CPC ......... A61B 6/54; A61B 6/025; A61B 6/4035; A61B 6/502; A61B 6/5217; A61B 6/482
See application file for complete search history.

(56) References Cited

U.S. PATENT DOCUMENTS

| | | | |
|---|---|---|---|
| 2007/0242797 A1* | 10/2007 | Stewart | A61B 6/482 378/16 |
| 2010/0020920 A1 | 1/2010 | Mertelmeier | |
| 2012/0224668 A1 | 9/2012 | Baetz et al. | |
| 2015/0294083 A1 | 10/2015 | Yokokubo | |
| 2017/0079601 A1 | 3/2017 | Hoernig et al. | |

FOREIGN PATENT DOCUMENTS

JP 2015-201092 A 11/2015

OTHER PUBLICATIONS

Extended European Search Report dated Jul. 22, 2022, issued in corresponding EP Patent Application No. 22157096.3.

* cited by examiner

*Primary Examiner* — Courtney D Thomas
(74) *Attorney, Agent, or Firm* — SOLARIS Intellectual Property Group, PLLC

(57) ABSTRACT

In tomosynthesis imaging which uses a radiation source that generates radiation and an Al filter and a Cu filter that change the quality of the radiation, irradiates a breast with the radiation emitted from the radiation source at a plurality of irradiation positions having different irradiation angles, and switches the Al filter and the Cu filter at each of the irradiation positions such that the radiation having different qualities is emitted to capture a plurality of radiographic images of the breast at each of the irradiation positions, a CPU performs control to set a last filter used at an n-th irradiation position as an initial filter used at an (n+1)-th irradiation position.

7 Claims, 11 Drawing Sheets

FIG. 5

| IMAGING | FIRST IRRADIATION POSITION | SECOND IRRADIATION POSITION | THIRD IRRADIATION POSITION | FOURTH IRRADIATION POSITION | FIFTH IRRADIATION POSITION | SIXTH IRRADIATION POSITION | SEVENTH IRRADIATION POSITION |
|---|---|---|---|---|---|---|---|
| FIRST | Al FILTER (LE) | Cu FILTER (HE) | Al FILTER (LE) | Cu FILTER (HE) | Al FILTER (LE) | Cu FILTER (HE) | Al FILTER (LE) |
| SECOND | Cu FILTER (HE) | Al FILTER (LE) | Cu FILTER (HE) | Al FILTER (LE) | Cu FILTER (HE) | Al FILTER (LE) | Cu FILTER (HE) |

FIG. 7A

| IRRADIATION | FIRST IRRADIATION POSITION | SECOND IRRADIATION POSITION | THIRD IRRADIATION POSITION | FOURTH IRRADIATION POSITION | FIFTH IRRADIATION POSITION | SIXTH IRRADIATION POSITION | SEVENTH IRRADIATION POSITION |
|---|---|---|---|---|---|---|---|
| FIRST | FIRST FILTER (LE) | SECOND FILTER (HE) | FIRST FILTER (LE) | SECOND FILTER (HE) | FIRST FILTER (LE) | SECOND FILTER (HE) | FIRST FILTER (LE) |
| SECOND | THIRD FILTER (ME) | THIRD FILTER (ME) | THIRD FILTER (ME) | THIRD FILTER (ME) | THIRD FILTER (ME) | THIRD FILTER (ME) | THIRD FILTER (ME) |
| THIRD | SECOND FILTER (HE) | FIRST FILTER (LE) | SECOND FILTER (HE) | FIRST FILTER (LE) | SECOND FILTER (HE) | FIRST FILTER (LE) | SECOND FILTER (HE) |

FIG. 7B

| IRRADIATION | FIRST IRRADIATION POSITION | SECOND IRRADIATION POSITION | THIRD IRRADIATION POSITION | FOURTH IRRADIATION POSITION | FIFTH IRRADIATION POSITION | SIXTH IRRADIATION POSITION | SEVENTH IRRADIATION POSITION |
|---|---|---|---|---|---|---|---|
| FIRST | FIRST FILTER (LE) | SECOND FILTER (HE) | THIRD FILTER (ME) | FIRST FILTER (LE) | SECOND FILTER (HE) | THIRD FILTER (ME) | FIRST FILTER (LE) |
| SECOND | THIRD FILTER (ME) | FIRST FILTER (LE) | SECOND FILTER (HE) | THIRD FILTER (ME) | FIRST FILTER (LE) | SECOND FILTER (HE) | THIRD FILTER (ME) |
| THIRD | SECOND FILTER (HE) | THIRD FILTER (ME) | FIRST FILTER (LE) | SECOND FILTER (HE) | THIRD FILTER (ME) | FIRST FILTER (LE) | SECOND FILTER (HE) |

FIG. 7C

| IRRADIATION | FIRST IRRADIATION POSITION | SECOND IRRADIATION POSITION | THIRD IRRADIATION POSITION | FOURTH IRRADIATION POSITION | FIFTH IRRADIATION POSITION | SIXTH IRRADIATION POSITION | SEVENTH IRRADIATION POSITION |
|---|---|---|---|---|---|---|---|
| FIRST | THIRD FILTER (ME) | SECOND FILTER (HE) | THIRD FILTER (ME) | SECOND FILTER (HE) | THIRD FILTER (ME) | SECOND FILTER (HE) | THIRD FILTER (ME) |
| SECOND | FIRST FILTER (LE) | FIRST FILTER (LE) | FIRST FILTER (LE) | FIRST FILTER (LE) | FIRST FILTER (LE) | FIRST FILTER (LE) | FIRST FILTER (LE) |
| THIRD | SECOND FILTER (HE) | THIRD FILTER (ME) | SECOND FILTER (HE) | THIRD FILTER (ME) | SECOND FILTER (HE) | THIRD FILTER (ME) | SECOND FILTER (HE) |

IMAGING CONTROL DEVICE, RADIOGRAPHY SYSTEM, IMAGING CONTROL METHOD, AND IMAGING CONTROL PROGRAM

CROSS-REFERENCE TO RELATED APPLICATIONS

The present application claims priority under 35 U.S.C. § 119 to Japanese Patent Application No. 2021-024604 filed on Feb. 18, 2021. The above application is hereby expressly incorporated by reference, in its entirety, into the present application.

BACKGROUND

1. Technical Field

The present disclosure relates to an imaging control device, a radiography system, an imaging control method, and an imaging control program.

2. Description of the Related Art

In general, so-called tomosynthesis imaging is known which irradiates an object with radiation at a plurality of irradiation positions having different irradiation angles to capture a plurality of radiographic images of the object at different irradiation positions.

In addition, in general, a technique is known which emits radiation a plurality of times at the same irradiation position of the radiation and captures a radiographic image whenever the radiation is emitted. As this type of technique, a technique is known which emits radiation with different energy levels and captures a radiographic image whenever the radiation is emitted. For example, dual energy subtraction imaging is given as an example of the technique. According to the dual energy subtraction imaging, a difference image between a first radiographic image captured by emitting radiation with first energy and a second radiographic image captured by emitting radiation with second energy different from the first energy is obtained.

Further, a technique is known which emits radiation a plurality of times at each irradiation position and captures a radiographic image whenever the radiation is emitted in the tomosynthesis imaging. For example, JP2015-201092A discloses a mammography apparatus that performs dual energy subtraction imaging in the tomosynthesis imaging.

SUMMARY

However, in general, a technique is known in which a radiography apparatus comprises a plurality of types of filters and captures a radiographic image using a filter selected from the plurality of types of filters. For example, the technique described in JP2015-201092A discloses a technique which makes a filter used in a case in which radiation with first energy is emitted different from a filter used in a case in which radiation with second energy is emitted. In a case in which the radiation is emitted a plurality of times at each irradiation position in the tomosynthesis imaging and the filter is switched whenever the radiation is emitted, there is a problem that the number of times the filter is switched increases.

The present disclosure has been made in view of the above-mentioned problems, and an object of the present disclosure is to provide an imaging control device, a radiography system, an imaging control method, and an imaging control program that can reduce the number of times a filter is switched in the entire tomosynthesis imaging in which images are captured a plurality of times at each of a plurality of irradiation positions.

In order to achieve the above object, according to a first aspect of the present disclosure, there is provided an imaging control device comprising at least one processor. In tomosynthesis imaging which uses a radiation source that generates radiation and a plurality of types of filters that change a quality of the radiation, irradiates an object with the radiation emitted from the radiation source at a plurality of irradiation positions having different irradiation angles, and switches the plurality of types of filters at each of the irradiation positions such that the radiation having different qualities is emitted to capture a plurality of radiographic images of the object at each of the irradiation positions, the processor performs control to set a last filter used at an n-th irradiation position as an initial filter used at an (n+1)-th irradiation position.

According to a second aspect of the present disclosure, in the imaging control device according to the first aspect, the plurality of types of filters may include a first filter that is used in a case in which radiation with first energy is emitted and a second filter that is used in a case in which radiation with second energy higher than the first energy is emitted, and the processor may perform control to use the first filter as the initial filter at an initial irradiation position among the plurality of irradiation positions.

According to a third aspect of the present disclosure, in the imaging control device according to the first aspect, the plurality of types of filters may be three or more filters that are used in a case in which radiation with different energy levels is emitted, and the processor may perform control to set a filter that is used in a case in which radiation with the lowest energy is emitted as the initial filter at an initial irradiation position among the plurality of irradiation positions.

In addition, in order to achieve the above object, according to a fourth aspect of the present disclosure, there is provided a radiography system comprising: a radiography apparatus that includes a radiation source which generates radiation and a plurality of types of filters which change energy of the radiation generated by the radiation source, irradiates an object with the radiation emitted from the radiation source at a plurality of irradiation positions having different irradiation angles, and switches the plurality of types of filters at each of the irradiation positions such that the radiation having different energy levels is emitted to capture a plurality of radiographic images of the object at each of the irradiation positions; and the imaging control device according to the present disclosure.

Further, in order to achieve the above object, according to a fifth aspect of the present disclosure, there is provided a radiography system comprising: a radiation source that generates radiation; a plurality of types of filters that change energy of the radiation generated by the radiation source; and a filter switching mechanism that, in a case in which a radiography apparatus irradiates an object with the radiation emitted from the radiation source at a plurality of irradiation positions having different irradiation angles and captures a plurality of radiographic images of the object obtained by the irradiation with the radiation having different energy levels at each of the irradiation positions, switches the plurality of types of filters at each of the irradiation positions and switches a last filter used at an n-th irradiation position to an initial filter used at an (n+1)-th irradiation position.

Furthermore, in order to achieve the above object, according to a sixth aspect of the present disclosure, there is provided an imaging control method executed by a computer. The imaging control method comprises, in tomosynthesis imaging which uses a radiation source that generates radiation and a plurality of types of filters that change a quality of the radiation, irradiates an object with the radiation emitted from the radiation source at a plurality of irradiation positions having different irradiation angles, and switches the plurality of types of filters at each of the irradiation positions such that the radiation having different qualities is emitted to capture a plurality of radiographic images of the object at each of the irradiation positions, performing control to set a last filter used at an n-th irradiation position as an initial filter used at an (n+1)-th irradiation position.

Moreover, in order to achieve the above object, according to a seventh aspect of the present disclosure, there is provided an imaging control program that causes a computer to perform a process of: in tomosynthesis imaging which uses a radiation source that generates radiation and a plurality of types of filters that change a quality of the radiation, irradiates an object with the radiation emitted from the radiation source at a plurality of irradiation positions having different irradiation angles, and switches the plurality of types of filters at each of the irradiation positions such that the radiation having different qualities is emitted to capture a plurality of radiographic images of the object at each of the irradiation positions, performing control to set a last filter used at an n-th irradiation position as an initial filter used at an (n+1)-th irradiation position.

According to the present disclosure, in the tomosynthesis imaging in which images are captured a plurality of times at each of a plurality of irradiation positions, it is possible to reduce the number of times the filter is switched in the entire tomosynthesis imaging.

BRIEF DESCRIPTION OF THE DRAWINGS

Exemplary embodiments according to the technique of the present disclosure will be described in detail based on the following figures, wherein:

FIG. 5 is a diagram illustrating a specific example of filters used for each imaging operation at each irradiation position in contrast imaging and tomosynthesis imaging performed in the mammography apparatus in the embodiment, FIG. 7A is a diagram illustrating an example of filters used for each imaging operation at each irradiation position in the contrast imaging and the tomosynthesis imaging performed in the mammography apparatus in a modification example, FIG. 7B is a diagram illustrating another example of the filters used for each imaging operation at each irradiation position in the contrast imaging and the tomosynthesis imaging performed in the mammography apparatus in the modification example, FIG. 7C is a diagram illustrating still another example of the filters used for each imaging operation at each irradiation position in the contrast imaging and the tomosynthesis imaging performed in the mammography apparatus in the modification example.

DETAILED DESCRIPTION

Hereinafter, an embodiment of the present disclosure will be described in detail with reference to the drawings. In addition, this embodiment does not limit the present disclosure. Further, in the following description, tomosynthesis imaging in a case in which contrast imaging is performed is given as an example of tomosynthesis imaging according to the present disclosure which irradiates an object with radiation having different qualities to capture a plurality of radiographic images at each irradiation position.

Figure 1:
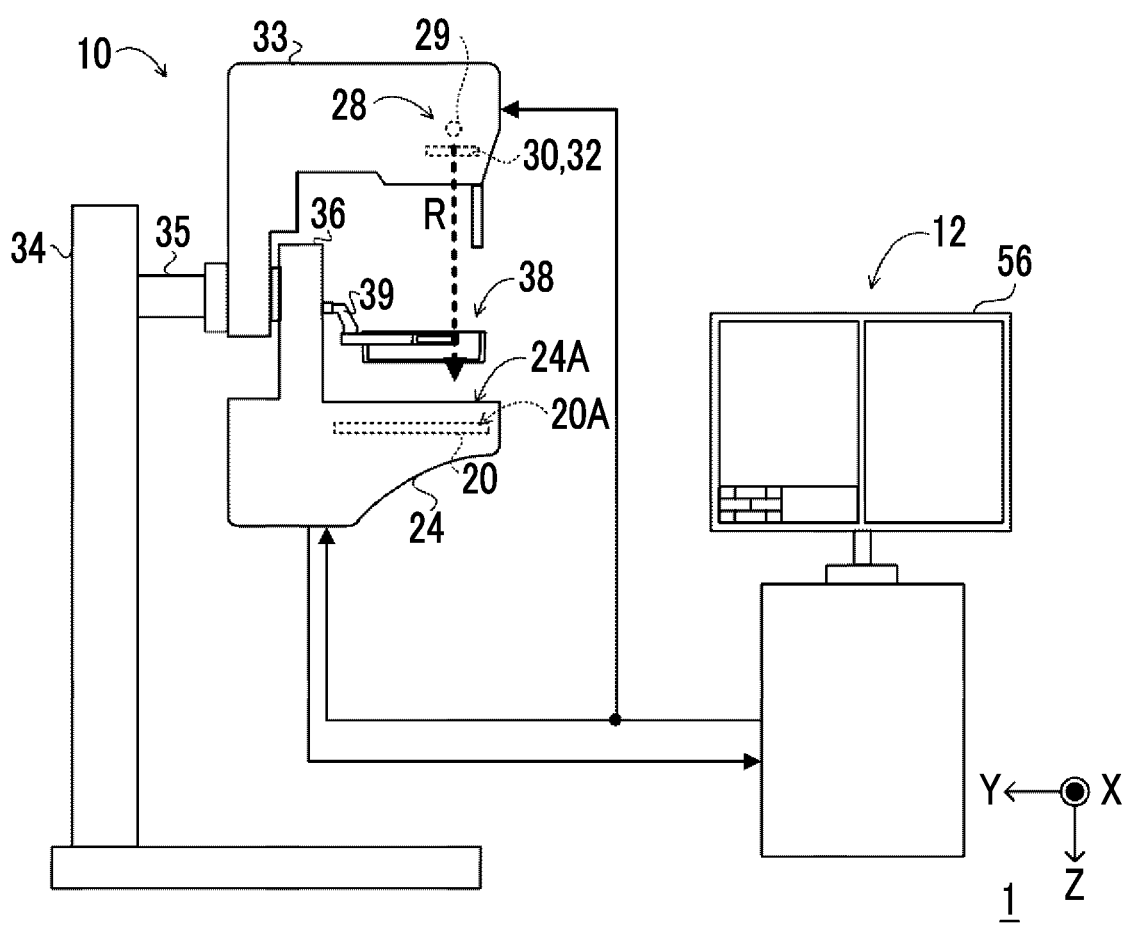
FIG. 1 is a diagram schematically illustrating an example of the overall configuration of a radiography system according to an embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12.

First, the mammography apparatus 10 according to this embodiment will be described. FIG. 1 is a side view illustrating an example of the outward appearance of the mammography apparatus 10 according to this embodiment. In addition, FIG. 1 illustrates an example of the outward appearance of the mammography apparatus 10 as viewed from the left side of the subject.

The mammography apparatus 10 according to this embodiment is an apparatus that irradiates the breast of the subject as an object with radiation R (for example, X-rays) to capture a radiographic image of the breast under the control of the console 12. In addition, the mammography apparatus 10 may be an apparatus that images the breast of the subject not only in a state in which the subject is standing (standing state) but also in a state in which the subject is sitting on, for example, a chair (including a wheelchair) (sitting state).

Further, the mammography apparatus 10 according to this embodiment has a function of performing two types of imaging, that is, so-called contrast imaging that captures images in a state in which a contrast medium is injected into the breast of the subject and general imaging. In addition, in this embodiment, imaging that is performed in a state in which the contrast medium injected into the breast of the subject is referred to as "contrast imaging", and imaging other than the contrast imaging is referred to as "general imaging". Furthermore, the mammography apparatus 10 according to this embodiment has a function of performing normal imaging that captures images at an irradiation position where a radiation source 29 is disposed along a normal direction to a detection surface 20A of a radiation detector 20 and so-called tomosynthesis imaging that captures images while moving the radiation source 29 to each of a plurality of irradiation positions. In addition, the mammography apparatus 10 can perform both the contrast imaging and the general imaging in both the normal imaging and the tomosynthesis imaging.

The radiation detector 20 detects the radiation R transmitted through the breast which is the object. Specifically, the radiation detector 20 detects the radiation R transmitted through the breast of the subject and an imaging table 24, generates a radiographic image on the basis of the detected radiation R, and outputs image data indicating the generated radiographic image. In the following description, the generation of a radiographic image by the radiation detector 20 may be referred to as "imaging". The type of the radiation detector 20 according to this embodiment is not particularly limited. For example, the radiation detector 20 may be an indirect-conversion-type radiation detector that converts the radiation R into light and converts the converted light into charge or a direct-conversion-type radiation detector that directly converts the radiation R into charge.

As illustrated in FIG. 1, the radiation detector 20 is disposed in the imaging table 24. In the mammography apparatus 10 according to this embodiment, in a case in which imaging is performed, the breast of the subject is positioned on an imaging surface 24A of the imaging table 24 by a user.

A compression plate 38 used to compress the breast in a case in which imaging is performed is attached to a compression unit 36 that is provided on the imaging table 24. Specifically, the compression unit 36 is provided with a compression plate driving unit (not illustrated) that moves the compression plate 38 in a direction (hereinafter, referred to as an "up-down direction") toward or away from the imaging table 24. A support portion 39 of the compression plate 38 is detachably attached to the compression plate driving unit and is moved in the up-down direction by the compression plate driving unit to compress the breast of the subject between the compression plate 38 and the imaging table 24.

A radiation emitting unit 28 comprises the radiation source 29 and a plurality of types of filters that change the quality of the radiation R. Each of the plurality of types of filters is used in the capture of radiographic images. The subject is irradiated with the radiation R transmitted through the filter, which makes it possible to reduce soft rays. Therefore, it is possible to suppress the radiation exposure dose of the subject. In this embodiment, an Al filter 30 and a Cu filter 32, which will be described in detail below, are provided as an example of the plurality of types of filters. As illustrated in FIG. 1, the radiation emitting unit 28 is provided in an arm portion 33. In addition, the type and number of the plurality of types of filters included in the radiation emitting unit 28 are not particularly limited, and at least one of the absorption rate of the radiation R transmitted by the filters, the attenuation rate of the radiation R transmitted by the filters, or an energy component of the radiation R absorbed by the filters may be different. For example, the plurality of types of filters are not limited to the Al filter 30 and the Cu filter 32 according to this embodiment and may include, for example, a silver (Ag) filter, a molybdenum (Mo) filter, a rhodium (Rh) filter, and a tin (Sn) filter. In addition, the plurality of types of filters may include filters that are made of the same material and have different thicknesses. Further, the plurality of types of filters may be various filters corresponding to, for example, the tube of the radiation source 29.

In addition, as illustrated in FIG. 1, the mammography apparatus 10 according to this embodiment comprises the imaging table 24, the arm portion 33, a base 34, and a shaft portion 35. The arm portion 33 is held by the base 34 so as to be movable in the up-down direction (Z-axis direction). Further, the arm portion 33 can be rotated with respect to the base 34 by the shaft portion 35. The shaft portion 35 is fixed to the base 34, and the shaft portion 35 and the arm portion 33 are rotated integrally.

Gears are provided in each of the shaft portion 35 and the compression unit 36 of the imaging table 24. The gears can be switched between an engaged state and a non-engaged state to switch between a state in which the compression unit 36 of the imaging table 24 and the shaft portion 35 are connected and rotated integrally and a state in which the shaft portion 35 is separated from the imaging table 24 and runs idle. In addition, components for switching between the transmission and non-transmission of the power of the shaft portion 35 are not limited to the gears, and various mechanical elements may be used.

Each of the arm portion 33 and the imaging table 24 can be relatively rotated with respect to the base 34, using the shaft portion 35 as a rotation axis. In this embodiment, engagement portions (not illustrated) are provided in each of the base 34, the arm portion 33, and the compression unit 36 of the imaging table 24. The state of the engagement portions is switched to connect each of the arm portion 33 and the compression unit 36 of the imaging table 24 to the base 34. One or both of the arm portion 33 and the imaging table 24 connected to the shaft portion 35 are integrally rotated on the shaft portion 35.

Figure 2:
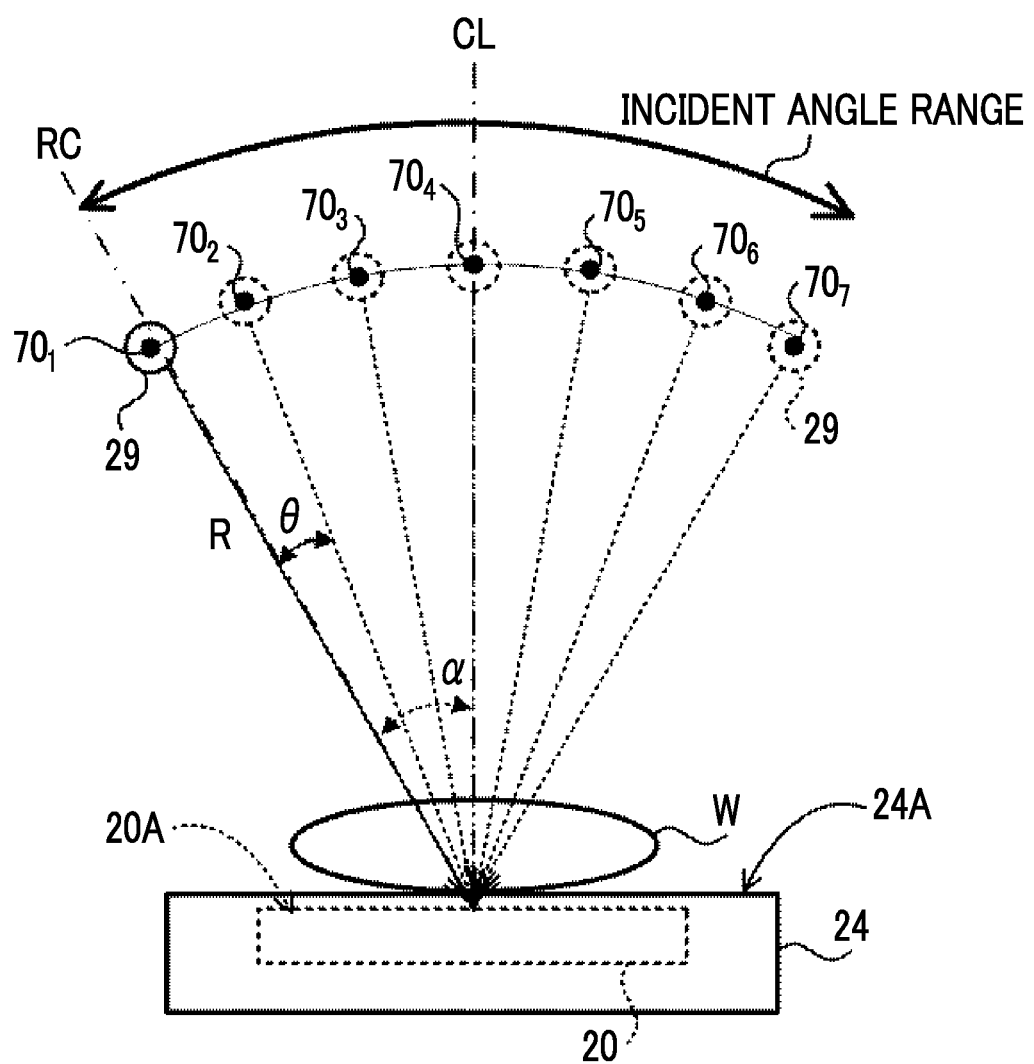
FIG. 2 is a diagram illustrating an example of tomosynthesis imaging.

In a case in which the tomosynthesis imaging is performed in the mammography apparatus 10, the radiation source 29 of the radiation emitting unit 28 is continuously moved to each of a plurality of irradiation positions having different irradiation angles by the rotation of the arm portion 33. FIG. 2 is a diagram illustrating an example of the tomosynthesis imaging. In addition, the compression plate 38 is not illustrated in FIG. 2. In this embodiment, as illustrated in FIG. 2, the radiation source 29 is moved to irradiation positions $70_k$ (k=1, 2, . . . ; the maximum value of k is 7 in FIG. 2) with different irradiation angles which are arranged at an interval of a predetermined angle θ, that is, positions where the radiation R is incident on the detection surface 20A of the radiation detector 20 at different angles. At each irradiation position $70_k$, the radiation R is emitted from the radiation source 29 to a breast W in response to an instruction from the console 12, and the radiation detector 20 captures a radiographic image. In the radiography system 1, in a case in which the tomosynthesis imaging that moves the radiation source 29 to each of the irradiation positions $70_k$ and captures radiographic images at each of the irradiation positions $70_k$ is performed, seven radiographic images are obtained in the example illustrated in FIG. 2. In addition, in the following description, in a case in which the radiographic images are generically referred to regardless of the types of radiographic images, such as low-energy images and high-energy images, which will be described below, they are simply referred to as "radiographic images". Further, in the following description, in a case in which the irradiation positions $70_k$ are generically referred to, a reference numeral k for distinguishing each irradiation position is omitted, and the irradiation positions $70_k$ are referred to as "irradiation positions 70". Furthermore, in a case in which each irradiation position $70_k$ is distinguished, the irradiation position is referred to as a "k-th irradiation position". For example, in FIG. 2, the first to seventh irradiation positions $70_1$ to $70_7$ are illustrated.

In addition, as illustrated in FIG. 2, the incident angle of the radiation R means an angle α formed between a normal line CL to the detection surface 20A of the radiation detector 20 and a radiation axis RC. The radiation axis RC manes an axis that connects the focus of the radiation source 29 at each irradiation position 70 and a preset position such as the center of the detection surface 20A. Further, here, it is assumed that the detection surface 20A of the radiation detector 20 is substantially parallel to the imaging surface 24A. Hereinafter, a predetermined range in which the incident angles are different in the tomosynthesis imaging as illustrated in FIG. 2 is referred to as an "incident angle range". A specific example of the incident angle range is a range of ±10 degrees or ±20 degrees with respect to the normal line CL to the detection surface 20A of the radiation detector 20. Furthermore, in this embodiment, the "incident angle" and the "irradiation angle" of the radiation R are synonymous.

On the other hand, in a case in which the mammography apparatus 10 performs the normal imaging, the radiation source 29 of the radiation emitting unit 28 remains at the irradiation position $70_k$ (the irradiation position $70_k$ along the normal direction, the irradiation position $70_4$ in FIG. 2) where the irradiation angle α is 0 degrees. The radiation R is emitted from the radiation source 29 in response to an instruction from the console 12, and the radiation detector 20 captures a radiographic image.

Figure 3:
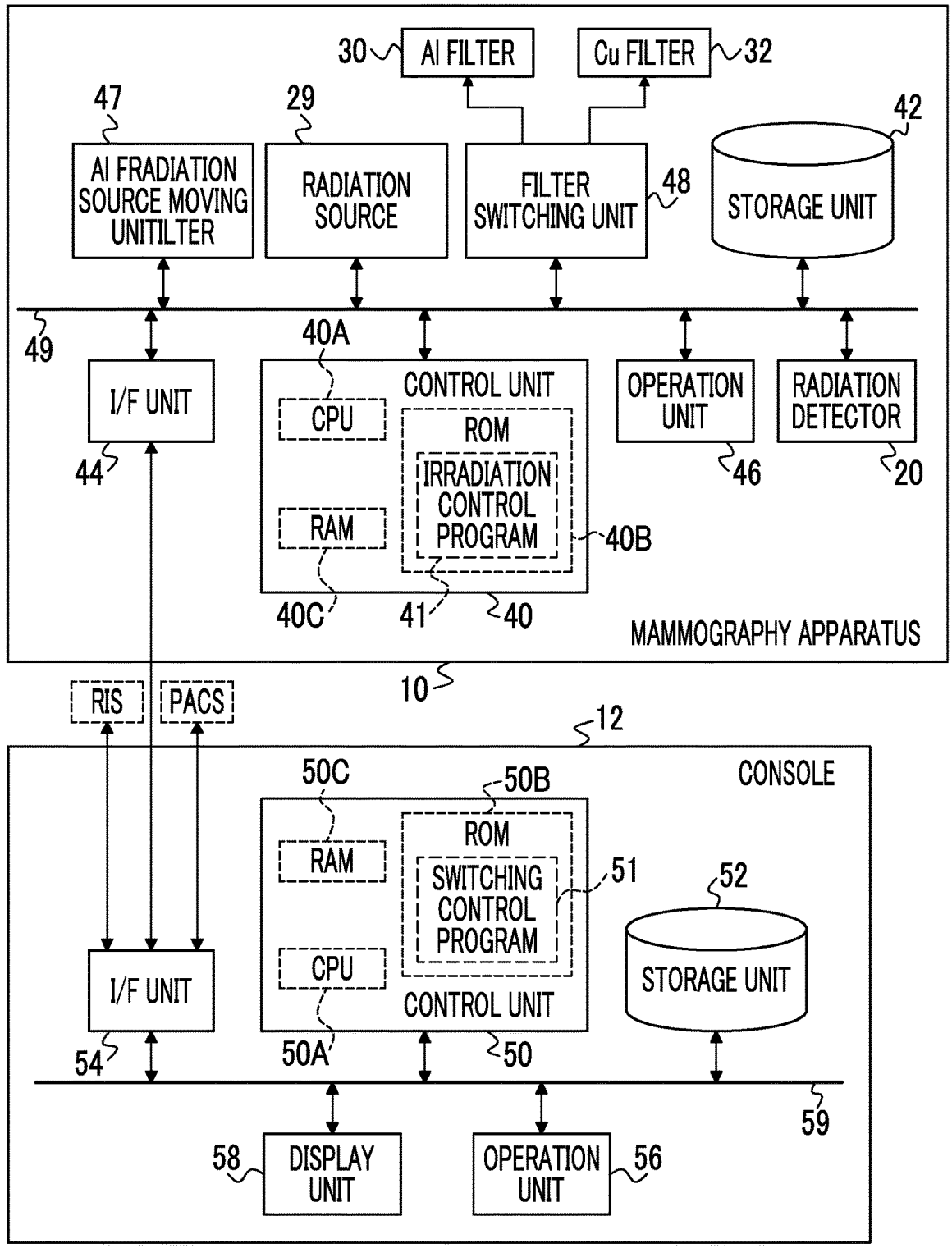
FIG. 3 is a block diagram illustrating an example of the configuration of a mammography apparatus and a console according to the embodiment.

Further, FIG. 3 is a block diagram illustrating an example of the configuration of the mammography apparatus 10 and the console 12 according to the embodiment. As illustrated in FIG. 3, the mammography apparatus 10 according to this embodiment further comprises a control unit 40, a storage unit 42, an interface (I/F) unit 44, an operation unit 46, a radiation source moving unit 47, and a filter switching unit 48. The control unit 40, the storage unit 42, the I/F unit 44, the operation unit 46, the radiation source moving unit 47, and the filter switching unit 48 are connected to each other through a bus 49, such as a system bus or a control bus, such that they can transmit and receive various kinds of information.

The control unit 40 controls the overall operation of the mammography apparatus 10 under the control of the console 12. The control unit 40 comprises a central processing unit (CPU) 40A, a read only memory (ROM) 40B, and a random access memory (RAM) 40C. The ROM 40B stores in advance various programs that are executed by the CPU 40A and include an imaging program for controlling the capture of radiographic images and an irradiation control program 41 for controlling the emission of radiation by the radiation source 29. The RAM 40C temporarily stores various kinds of data.

For example, image data of the radiographic image captured by the radiation detector 20 and various other kinds of information are stored in the storage unit 42. A specific example of the storage unit 42 is a hard disk drive (HDD), a solid state drive (SSD), or the like. The I/F unit 44 transmits and receives various kinds of information to and from the console 12 using wireless communication or wired communication. The image data of the radiographic image captured by the radiation detector 20 in the mammography apparatus 10 is transmitted to the console 12 through the I/F unit 44 by wireless communication or wired communication.

Each of the control unit 40, the storage unit 42, and the I/F unit 44 according to this embodiment is provided in the imaging table 24.

In addition, the operation unit 46 is provided as a plurality of switches in, for example, the imaging table 24 of the mammography apparatus 10. Further, the operation unit 46 may be provided as a touch panel switch or may be provided as a foot switch that is operated by the feet of the user such as a doctor or a radiology technician.

The radiation source moving unit 47 has a function of moving the radiation source 29 to each of the plurality of irradiation positions 70 under the control of the control unit 40 in a case in which the tomosynthesis imaging is performed as described above. Specifically, the radiation source moving unit 47 rotates the arm portion 33 with respect to the imaging table 24 to move the radiation source 29 to each of the plurality of irradiation positions 70. The radiation source moving unit 47 according to this embodiment is provided inside the arm portion 33.

The filter switching unit 48 has a function of switching the filter used in a case in which the radiation R is emitted from the radiation source 29 to either the Al filter 30 or the Cu filter 32 in response to an instruction from the console 12. In the mammography apparatus 10 according to this embodiment, in a case in which a radiographic image is captured, the breast of the subject is irradiated with the radiation R that has been emitted from the radiation source 29 and transmitted through at least one of the Al filter 30 or the Cu filter 32. Therefore, the filter switching unit 48 switches the filter used to capture a radiographic image to the Al filter 30 or the Cu filter 32 according to, for example, the type of imaging. Specifically, the filter switching unit 48 has a function of switching the filter inserted into the irradiation field of the radiation R emitted from the radiation source 29 to at least one of the Al filter 30 or the Cu filter 32. The specific configuration of the filter switching unit 48 is not particularly limited. For example, a gear is provided in a holding member that holds each of the Al filter 30 and the Cu filter 32, and the filter switching unit 48 rotates a gear that is engaged with the gear provided in the holding member to move the Al filter 30 and the Cu filter 32 arranged in the left-right direction of the mammography apparatus 10 between the inside of the irradiation field and the outside of the irradiation field, thereby switching the filter inserted into the irradiation field of the radiation R. In addition, the filter switching unit 48 according to this embodiment is included in the radiation emitting unit 28 together with the radiation source 29, the Al filter 30, and the Cu filter 32 and is provided in the arm portion 33.

On the other hand, the console 12 according to this embodiment has a function of controlling the mammography apparatus 10 using, for example, an imaging order and various kinds of information acquired from a radiology information system (RIS) through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. Various programs which are executed by the CPU 50A and include a switching control program 51 are stored in the ROM 50B in advance. The RAM 50C temporarily stores various kinds of data. In this embodiment, the CPU 50A is an example of a processor according to the present disclosure, and the console 12 is an example of an imaging control device according to the present disclosure. Further, in this embodiment, the switching control program 51 is an example of an imaging control program according to the present disclosure.

For example, the image data of the radiographic image captured by the mammography apparatus 10 and various other kinds of information are stored in the storage unit 52. A specific example of the storage unit 52 is an HDD, an SSD, or the like.

The operation unit 56 is used by the user to input instructions, which are related to, for example, the capture of a radiographic image and include an instruction to emit the radiation R, various kinds of information, and the like. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information among the mammography apparatus 10, the RIS, and a picture archiving and communication system (PACS) using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
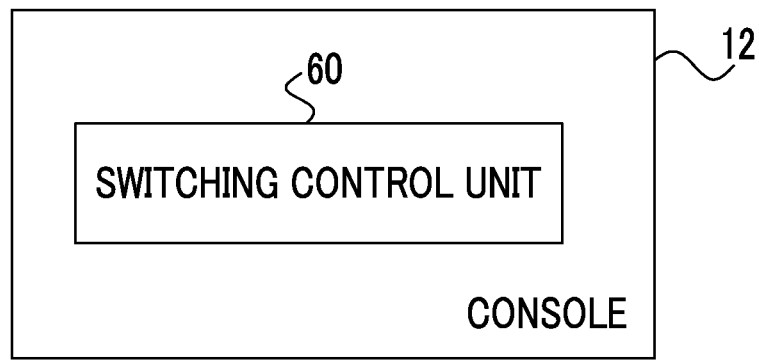
FIG. 4 is a functional block diagram illustrating an example of the functions of the console according to the embodiment.

As described above, the console 12 according to this embodiment has a function of performing control to switch the filter used to capture a radiographic image to either the Al filter 30 or the Cu filter 32 using the filter switching unit 48 of the mammography apparatus 10. FIG. 4 illustrates a functional block diagram illustrating an example of a configuration related to the switching of the filter, which is used to capture a radiographic image in the mammography apparatus 10, in the console 12 according to this embodiment. As illustrated in FIG. 4, the console 12 comprises a switching control unit 60. For example, in the console 12 according to this embodiment, the CPU 50A of the control unit 50 executes the switching control program 51 stored in the ROM 50B to function as the switching control unit 60.

The switching control unit 60 according to this embodiment switches the filter used to capture a radiographic image to the Al filter 30 or the Cu filter 32 in a case in which the contrast imaging and the tomosynthesis imaging are performed in the mammography apparatus 10.

In a case in which the contrast imaging is performed, for example, radiographic images are captured twice using the radiation R with two types of energy. One imaging operation is to irradiate the breast, into which the contrast medium has been injected, with radiation with first energy emitted from the radiation source 29 to capture a radiographic image. The other imaging operation is to irradiate the breast, into which the contrast medium has been injected, with radiation with second energy higher than the first energy emitted from the radiation source 29 to capture a radiographic image. In addition, in this embodiment, the radiographic image captured by emitting the radiation R with the first energy is referred to as a "low-energy image", and the radiographic image captured by emitting the radiation R with the second energy is referred to as a "high-energy image".

For example, an iodine contrast medium having a k-edge of 32 keV is generally used as the contrast medium used for the contrast imaging. In this case, in the contrast imaging, the radiation R with the first energy lower than the k-edge of the iodine contrast medium is emitted to capture the low-energy image. The Al filter 30 is used to capture the low-energy image. The quality of the radiation R emitted to the breast can be the first energy by the use of the Al filter 30.

Further, in the contrast imaging, the radiation R with the second energy higher than the k-edge of the iodine contrast medium is emitted to capture the high-energy image. The Cu filter 32 is used to capture the high-energy image. The quality of the radiation R emitted to the subject can be the second energy by the use of the Cu filter 32.

In addition, radiation absorption characteristics are different between the contrast media and the body tissues such as the mammary glands. Therefore, in the high-energy image captured as described above, the body tissues, such as the mammary glands and fat, are shown and the contrast medium is clearly shown. Further, in the low-energy image, the contrast medium is hardly shown, and the body tissues, such as the mammary glands, are clearly shown. Therefore, a difference image indicating the difference between the low-energy image and the high-energy image can be an image in which a mammary gland structure has been removed and the contrast medium is clearly shown.

In the case of the contrast imaging and the tomosynthesis imaging, two imaging operations, that is, an imaging operation of emitting the radiation R with the first energy using the Al filter 30 to capture the low-energy image and an imaging operation of emitting the radiation R with the second energy using the Cu filter 32 to capture the high-energy image are performed at each of the plurality of irradiation positions 70.

Therefore, the switching control unit 60 performs control to switch the filter inserted into the irradiation field to the Al filter 30 or the Cu filter 32 while the two imaging operations are performed at each of the plurality of irradiation positions 70. Further, the switching control unit 60 according to this embodiment performs control to set the filter used for a second imaging operation at an n-th irradiation position 70 as the filter used for a first imaging operation at an (n+1)-th irradiation position 70.

FIG. 5 illustrates a specific example of the filter used for each imaging operation at each irradiation position 70 in the contrast imaging and the tomosynthesis imaging. In the example illustrated in FIG. 5, information indicating the relationship between the filter used for the first imaging operation and the filter used for the second imaging operation at each of the first to seventh irradiation positions $70_1$ to $70_7$ is illustrated. As illustrated in FIG. 5, at the first irradiation position $70_1$ which is a start position of the tomosynthesis imaging, in the first imaging operation, the radiation R with the first energy (LE) is emitted using the Al filter 30 to capture the low-energy image. In addition, in the second imaging operation, the radiation R with the second energy (HE) is emitted using the Cu filter 32 to capture the high-energy image. Therefore, the switching control unit 60 performs control to switch the filter inserted into the irradiation field from the Al filter 30 to the Cu filter 32 between the first imaging operation and the second imaging operation.

At the next second irradiation position $70_2$, in the first imaging operation, the radiation R with the second energy (HE) is emitted using the Cu filter 32 to capture the high-energy image. Further, in the second imaging operation, the radiation R with the first energy (LE) is emitted using the Al filter 30 to capture the low-energy image. Therefore, the switching control unit 60 performs control to switch the filter inserted into the irradiation field from the Cu filter 32 to the Al filter 30 between the first imaging operation and the second imaging operation.

Furthermore, at the next third irradiation position $70_3$, in the first imaging operation, the radiation R with the first energy (LE) is emitted using the Al filter 30 to capture the low-energy image. In addition, in the second imaging operation, the radiation R with the second energy (HE) is emitted using the Cu filter 32 to capture the high-energy image. Therefore, the switching control unit 60 performs control to switch the filter inserted into the irradiation field from the Al filter 30 to the Cu filter 32 between the first imaging operation and the second imaging operation.

As described above, the switching control unit 60 according to this embodiment performs control to set the filter used for the second imaging operation at the n-th irradiation position 70 as the filter used for the first imaging operation at the (n+1)-th irradiation position 70. Therefore, the filter is not switched in a case in which the irradiation position 70 is changed.

Next, the operation of the console 12 in the contrast imaging and the tomosynthesis imaging by the radiography system 1 according to this embodiment will be described with reference to the drawings.

In a case in which the contrast imaging is performed, the user positions the breast, into which the contrast medium has been injected, on the imaging table 24 of the mammography apparatus 10 and compresses the breast with the compression plate 38.

Figure 6:
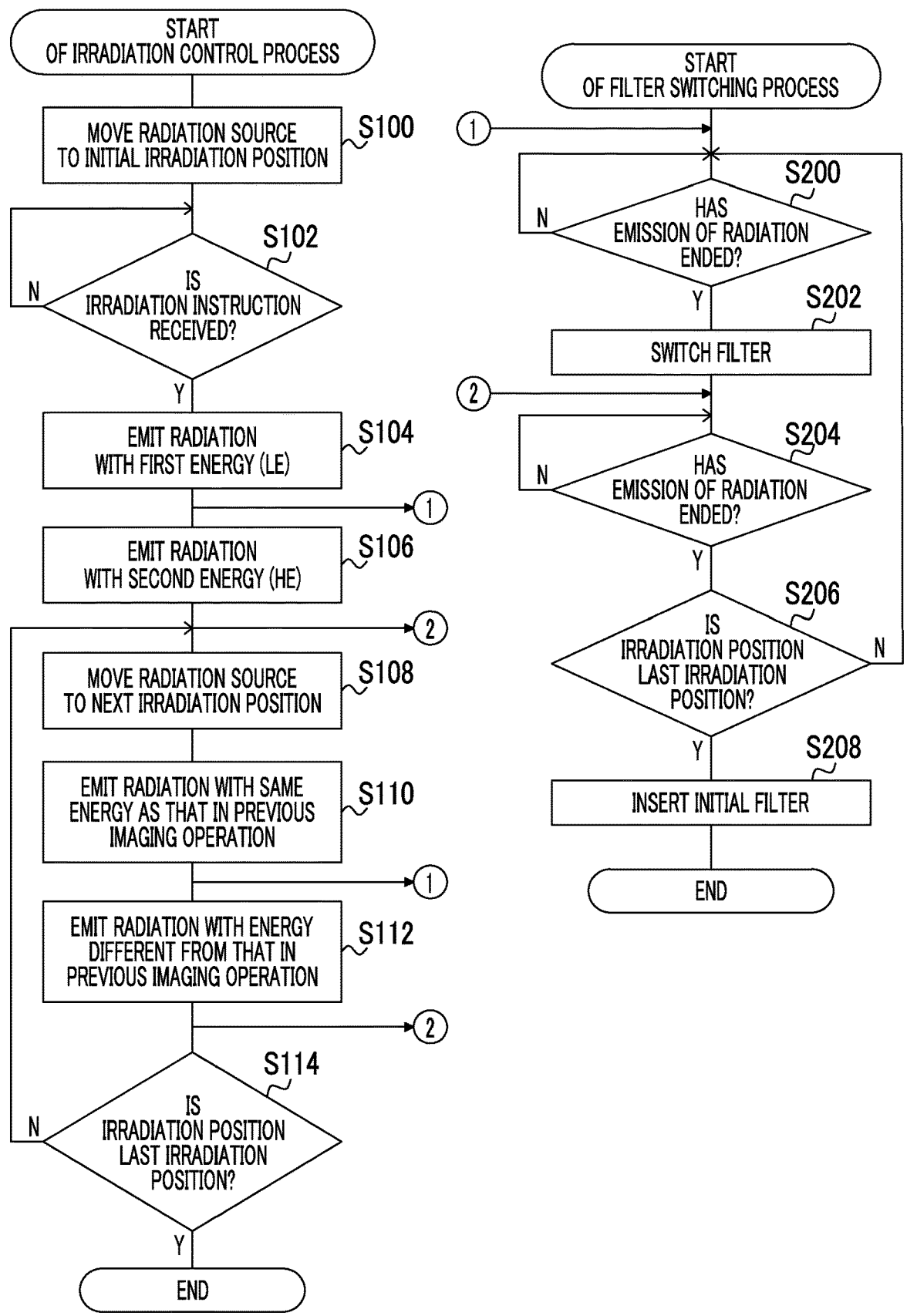
FIG. 6 is a flowchart illustrating an example of the flow of an irradiation control process by the mammography apparatus and an example of the flow of a filter switching process by the console in the embodiment.

In a case in which the contrast imaging and the tomosynthesis imaging are performed, the mammography apparatus 10 performs an irradiation control process to move the radiation source 29 to each irradiation position 70 and to capture the low-energy image and the high-energy image at each irradiation position 70. For example, the mammography apparatus 10 performs the irradiation control process in a case in which an instruction to perform the contrast imaging and the tomosynthesis imaging is received from the console 12. FIG. 6 is a flowchart illustrating an example of the flow of the irradiation control process by the mammography apparatus 10 according to this embodiment. In the mammography apparatus 10 according to this embodiment, for example, the CPU 40A of the control unit 40 executes the irradiation control program 41 stored in the ROM 40B to perform the irradiation control process whose example is illustrated in FIG. 6.

In Step S100 of the irradiation control process illustrated in FIG. 6, the control unit 40 performs control to move the radiation source 29 to the initial irradiation position 70. Specifically, the control unit 40 directs the radiation source moving unit 47 to rotate the arm portion 33 such that the radiation source 29 is moved to the first irradiation position $70_1$ which is the initial irradiation position 70. In addition, the movement of the radiation source 29 to the initial irradiation position 70 may be performed before the breast is positioned on the imaging table 24.

Then, in Step S102, the control unit 40 determines whether or not an instruction to emit the radiation R is received. The determination result in Step S102 is "No" until the irradiation instruction is received. On the other hand, in a case in which the irradiation instruction is received, the determination result in Step S102 is "Yes", and the process proceeds to Step S104.

In Step S104, the control unit 40 performs control to emit the radiation R with the first energy. For example, in this embodiment, the mAs value set in the radiation source 29 is different between a case in which the radiation R with the first energy is emitted and a case in which the radiation R with the second energy is emitted. Therefore, the control unit 40 directs the radiation source 29 to emit the radiation R to the breast into which the contrast agent has been injected in a state in which the mAs value for emitting the radiation R with the first energy is set in the radiation source 29. The radiation detector 20 captures the low-energy image. Further, for example, whenever the emission of the radiation R ends, the mammography apparatus 10 according to this embodiment transmits irradiation end information indicating that the emission of the radiation R has ended to the console 12 through the I/F unit 44. Therefore, in a case in which the emission of the radiation R with the first energy by the process in Step S104 has ended, the control unit 40 transmits the irradiation end information to the mammography apparatus 10.

Then, in Step S106, the control unit 40 performs control to emit the radiation R with the second energy. The control unit 40 directs the radiation source 29 to emit the radiation R to the breast into which the contrast agent has been injected in a state in which the mAs value for emitting the radiation R with the second energy is set in the radiation source 29. The radiation detector 20 captures the high-energy image. Further, in a case in which the emission of the radiation R with the second energy by the process in Step S106 has ended, the control unit 40 transmits the irradiation end information to the mammography apparatus 10.

Then, in Step S108, the control unit 40 performs control to move the radiation source 29 to the next irradiation position 70. Specifically, as in Step S100, the control unit 40 directs the radiation source moving unit 47 to rotate the arm portion 33 such that the radiation source 29 is moved to the next irradiation position 70. For example, after the capture of the low-energy image and the high-energy image at the first irradiation position $70_1$ ends, the control unit 40 performs control to move the radiation source 29 to the second irradiation position $70_2$ which is the next irradiation position 70. In this embodiment, the radiation R is emitted at each irradiation position 70 in a state in which the movement of the radiation source 29 is stopped. Therefore, in a case in which the radiation source 29 reaches the next irradiation position 70, the control unit 40 stops the movement of the radiation source 29.

Then, in Step S110, the control unit 40 performs control to emit the radiation R having the same energy as that in the previous imaging operation. In other words, since the first imaging operation is performed at the irradiation position 70, the control unit 40 performs control to emit the radiation R having the same energy as the radiation R emitted at the previous irradiation position 70 in the second imaging operation. As illustrated in FIG. 5, for example, in a case in which the previous irradiation position 70 is the first irradiation position $70_1$, the control unit 40 performs control to emit the radiation R with the second energy and directs the radiation detector 20 to capture the high-energy image. Further, for example, in a case in which the previous irradiation position 70 is the second irradiation position $70_2$, the control unit 40 performs control to emit the radiation R with the first energy and directs the radiation detector 20 to capture the low-energy image. Furthermore, in a case in which the emission of the radiation R having the same energy as that in the previous imaging operation by the process in Step S110 has ended, the control unit 40 transmits the irradiation end information to the mammography apparatus 10 as described above.

Then, in Step S112, the control unit 40 performs control to emit the radiation R with energy different from that in the previous imaging operation. In other words, since the second imaging operation is performed at the irradiation position 70, the control unit 40 performs control to emit the radiation R having energy different from that of the radiation R emitted in the first imaging operation. In addition, in a case in which the emission of the radiation R having energy different from that in the previous imaging operation by the process in Step S112 has ended, the control unit 40 transmits the irradiation end information to the mammography apparatus 10 as described above.

As illustrated in FIG. 5, for example, in the case of the second irradiation position $70_2$, the radiation R with the first energy is emitted, and the radiation detector 20 captures the low-energy image. Further, for example, in a case in which the irradiation position 70 is the third irradiation position $70_3$, the radiation R with the second energy is emitted, and the radiation detector 20 captures the high-energy image.

Then, in Step S114, the control unit 40 determines whether or not the irradiation position 70 is the last irradiation position 70. In the example illustrated in FIGS. 2 and 5, in a case in which the irradiation position 70 is an irradiation position other than the irradiation position $70_7$, in other words, in a case in which the irradiation position 70 is one of the irradiation positions $70_1$ to $70_6$, the determination result in Step S114 is "No", and the process returns to Step S108. Then, the processes in Steps S108 to S112 are repeated. On the other hand, in a case in which the irradiation position 70 is the irradiation position $70_7$, the determination result in Step S114 is "Yes", and the irradiation control process illustrated in FIG. 6 ends.

On the other hand, in a case in which the contrast imaging and the tomosynthesis imaging are performed, the console 12 performs the filter switching process in order to perform control to switch the filter inserted into the irradiation field in the radiation emitting unit 28 of the mammography apparatus 10 as described above. For example, in a case in which the imaging menu acquired from the RIS includes an instruction to perform the contrast imaging and the tomosynthesis imaging, the console 12 performs the filter switching process. FIG. 6 is a flowchart illustrating an example of the flow of the filter switching process by the console 12 according to this embodiment. In the mammography apparatus 10 according to this embodiment, for example, the CPU 50A of the control unit 50 executes the switching control program 51 stored in the ROM 50B to perform the filter switching process whose example is illustrated in FIG. 6. Therefore, the CPU 50A of the control unit 50 functions as the switching control unit 60. Further, in this embodiment, in a case in which the contrast imaging and the tomosynthesis imaging are started, the Al filter 30 is inserted in the irradiation field. In addition, the filter inserted into the irradiation field in a case in which imaging is started as described above is referred to as an "initial filter".

In Step S200 of the filter switching process illustrated in FIG. 6, the switching control unit 60 determines whether or not the emission of the radiation R has ended in the mammography apparatus 10. In other words, the switching control unit 60 determines whether or not the emission of the radiation R in the first imaging operation has ended. Specifically, the switching control unit 60 determines whether or not either the emission of the radiation R with the first energy in Step S104 and the emission of the radiation R having the same energy as that in the previous imaging operation in Step S110 in the above-mentioned irradiation control process has ended.

For example, in this embodiment, as described above, whenever the emission of the radiation R ends, the mammography apparatus 10 transmits the irradiation end information indicating that the emission of the radiation R has ended to the console 12. Therefore, in a case in which the irradiation end information is received odd-numbered times after the start of the filter switching process, the switching control unit 60 according to this embodiment determines that the emission of the radiation R has ended. In addition, the method by which the switching control unit 60 determines whether or not the emission of the radiation R has ended in the mammography apparatus 10 is not limited to this aspect. For example, the irradiation time of the radiation R and the movement time of the radiation source 29 to each irradiation position 70 may be predetermined, and the switching control unit 60 may count the time elapsed since the start of the emission of the radiation R at the first irradiation position 70 and determine that the emission of the radiation R has ended at the timing when the irradiation time of the radiation R ends.

The determination result in Step S200 is "No" until the emission of the radiation R ends. On the other hand, in a case in which the emission of the radiation R ends, the determination result in Step S200 is "Yes", and the process proceeds to Step S202.

In Step S202, the switching control unit 60 performs control to switch the filter used for imaging. In other words, the switching control unit 60 performs control to switch the filter inserted into the irradiation field from the filter used for the first imaging operation to the filter used for the second imaging operation. Specifically, the switching control unit 60 performs control to transmit a switching instruction to switch the filter to the mammography apparatus 10, thereby switching the filter. In the mammography apparatus 10, in a case in which the switching instruction is received from the console 12, the control unit 40 directs the filter switching unit 48 to switch the filter inserted into the irradiation field. As illustrated in FIG. 5, for example, in a case in which the emission of the radiation R at the first irradiation position $70_1$ in the first imaging operation ends, the switching control unit 60 performs control to change the filter used for imaging from the Al filter 30 to the Cu filter 32. In the mammography apparatus 10, the radiation R with the second energy is emitted in the second imaging operation at the first irradiation position $70_1$ using the Cu filter 32 inserted into the irradiation field by the above-mentioned control, and the radiation detector 20 captures the high-energy image. Further, for example, in a case in which the emission of the radiation R at the second irradiation position $70_2$ in the first imaging operation ends, the switching control unit 60 performs control to switch the filter used for imaging from the Cu filter 32 to the Al filter 30. In the mammography apparatus 10, the radiation R with the first energy is emitted in the second imaging operation at the second irradiation position $70_2$ using the Al filter 30 inserted into the irradiation field by the above-mentioned control, and the radiation detector 20 captures the low-energy image.

Then, in Step S204, the switching control unit 60 determines whether or not the emission of the radiation R has ended in the mammography apparatus 10. In other words, the switching control unit 60 determines whether or not the emission of the radiation R in the second imaging operation has ended. Specifically, the switching control unit 60 determines whether or not either the emission of the radiation R with the second energy in S106 and the emission of the radiation R with energy different from that in the previous imaging operation in Step S112 in the above-mentioned irradiation control process has ended. As described above, in a case in which the irradiation end information is received even-numbered times after the start of the filter switching process, the switching control unit 60 according to this embodiment determines that the emission of the radiation R has ended. In addition, the method by which the switching control unit 60 determines whether or not the emission of the radiation R has ended in the mammography apparatus 10 is not limited to this aspect and may be, for example, the same as or different from that in Step S200.

The determination result in Step S204 is "No" until the emission of the radiation R ends. On the other hand, in a case in which the emission of the radiation R ends, the determination result in Step S204 is "Yes", and the process proceeds to Step S206.

In Step S206, the switching control unit 60 determines whether or not the irradiation position 70 of the radiation source 29 that has ended the emission of the radiation R is the last irradiation position 70. In the example illustrated in FIGS. 2 and 5, in a case in which the irradiation position 70 is an irradiation position other than the irradiation position $70_7$, in other words, in a case in which the irradiation position 70 is one of the irradiation positions $70_1$ to $70_6$, the determination result in Step S206 is "No", and the process returns to Step S200. Then, the processes in Steps S200 to S204 are repeated. On the other hand, in a case in which the irradiation position 70 is the irradiation position $70_7$, the determination result in Step S206 is "Yes", and the process proceeds to Step S208.

In Step S208, the switching control unit 60 performs control such that the initial filter is inserted into the irradiation field. In a case in which the total number of irradiation positions 70 in the contrast imaging and the tomosynthesis imaging is an odd number as in the example illustrated in FIGS. 2 and 5, the filter used for the second imaging operation at the last irradiation position 70 (the Cu filter 32 in FIG. 5) is different from the initial filter (the Al filter 30 in FIG. 5). Therefore, in a case in which the total number of irradiation positions 70 is an odd number, the switching control unit 60 performs control to switch the filter currently inserted into the irradiation field to the initial filter such that the initial filter is inserted into the irradiation field. Further, unlike the example illustrated in FIGS. 2 and 5, in a case in which the total number of irradiation positions 70 in the contrast imaging and the tomosynthesis imaging is an even number, the filter used for the second imaging operation at the last irradiation position 70 is the same as the initial filter. Therefore, in a case in which the total number of irradiation positions 70 is an even number, the switching control unit 60 keeps the filter currently inserted into the irradiation field as it is such that the initial filter is inserted into the irradiation field. In a case in which the process in Step S208 ends, the filter switching process illustrated in FIG. 6 ends.

As described above, in a case in which the contrast imaging and the tomosynthesis imaging are performed in this embodiment, the switching control unit 60 performs control to switch the filter used for the second imaging operation at the n-th irradiation position 70 to the filter used for the first imaging operation at the (n+1)-th irradiation position 70. Therefore, the switching control unit 60 does not switch the filter in a case in which the irradiation position 70 is changed.

Therefore, according to the console 12 of this embodiment, in the contrast imaging and the tomosynthesis imaging, it is possible to reduce the number of times the filter is switched in the entire tomosynthesis imaging.

As described above, in the radiography system 1 according to this embodiment, the contrast imaging and the tomosynthesis imaging are performed to obtain a plurality of low-energy images and a plurality of high-energy images. A difference tomographic image is generated by the image processing device from a plurality of low-energy images and high-energy images obtained by the image processing device and is used by the user to observe, for example, the contrast medium or the breast tissues. Any devices, such as the console 12 and various devices outside the radiography system 1, can be applied to the image processing device in this case. In addition, the "difference tomographic image" is a difference image and means a tomographic image.

Further, a method for generating the difference tomographic image in the image processing device is not limited. For example, difference images may be generated at each irradiation position 70, and a difference tomographic image may be generated from a series of the generated difference images. Specifically, the image processing device subtracts image data obtained by multiplying the low-energy image by a predetermined coefficient from image data obtained by multiplying the high-energy image by a predetermined coefficient for each corresponding pixel to generate difference image data indicating a difference image. Further, the image processing device reconstructs a series of difference images generated at each irradiation position 70 and generates a series of tomographic images having a predetermined slice thickness as the difference tomographic image. In addition, the method by which the image processing device generates the tomographic image is not particularly limited. For example, the reconstruction may be performed by a back projection method, such as a filter back projection (FBP) method or an iterative reconstruction method, or a known technique may be applied. Further, the slice thickness of the generated tomographic image is not particularly limited and may be determined according to, for example, the size of an object of interest, the quality of a radiographic image, the processing load of an arithmetic process in the generation, and instructions from the user.

Further, for example, a low-energy tomographic image may be generated from a plurality of low-energy images, a high-energy tomographic image may be generated from a plurality of high-energy images, and a difference image between the generated high-energy tomographic image and the generated low-energy tomographic image may be generated. Specifically, the image processing device generates tomographic images from a plurality of low-energy images captured at the plurality of irradiation positions 70 as described above to generate a series of low-energy tomographic images and generates tomographic images from a plurality of high-energy images captured at the plurality of irradiation positions 70 as described above to generate a series of high-energy tomographic images. Furthermore, the image processing device generates a difference image between the high-energy tomographic image and the low-energy tomographic image at the same slice position as described above to generate a difference tomographic image.

In either case, the generated difference tomographic image is an image in which the mammary gland structure has been removed and the contrast medium is clearly shown.

In addition, in this embodiment, the aspect has been described in which the switching control unit 60 performs control to use, as the initial filter, the Al filter 30 used in a case in which the radiation R with the first energy is emitted at the first irradiation position $70_1$ among the plurality of irradiation positions 70. In other words, the aspect in which the initial imaging at the first irradiation position $70_1$ among the plurality of irradiation positions 70 is the capture of the low-energy image has been described. However, the initial imaging at the first irradiation position $70_1$ is not limited to the capture of the low-energy image. In this embodiment, the initial imaging at the first irradiation position $70_1$ may be the capture of the high-energy image.

In addition, in a case in which a high-energy image is captured at each irradiation position 70 and then a low-energy image is captured, an afterglow is likely to occur in the low-energy image captured later due to the high-energy image captured first. As described above, in a case in which the initial imaging at the first irradiation position $70_1$ among the plurality of irradiation positions 70 is the capture of the low-energy image, for the plurality of irradiation positions 70, the number of irradiation positions 70 where the high-energy images are captured after the low-energy images are captured can be equal to or greater than the number of irradiation positions 70 where the low-energy images are captured after the high-energy images are captured. Therefore, in a case in which the Al filter 30 used to capture the low-energy image is used as the initial filter at the first irradiation position $70_1$ among the plurality of irradiation positions 70, it is possible to suppress the influence of the afterglow occurring in the low-energy image.

Modification Example 1

In the above-described embodiment, the aspect in which the mammography apparatus 10 comprises two types of filters, that is, the Al filter 30 and the Cu filter 32 as a plurality of types of filters and switches the filter between the Al filter 30 and the Cu filter 32 has been described. However, the mammography apparatus 10 may comprise three or more types of filters, sequentially switch the three or more types of filters at each irradiation position 70 in the contrast imaging and the tomosynthesis imaging, and emit the radiation R three times to capture three radiographic images.

As an example of this case, the aspect in which the radiation R with three types of energy is sequentially emitted at each irradiation position 70 to capture three radiographic images will be described. In addition, the aspect in which the lowest first energy (LE), the highest second energy (HE), and third energy (ME) that is higher than the first energy and lower than the second energy are used as three types of energy of the radiation R to be emitted will be described.

In this embodiment, at each irradiation position 70, the radiation R with the first energy is emitted using a first filter to capture a low-energy image. In addition, at each irradiation position 70, the radiation R with the third energy is emitted using a third filter to capture a medium-energy image. Further, at each irradiation position 70, the radiation R with the second energy is emitted using a second filter to capture a high-energy image.

FIG. 7A illustrates an example of the filters used for each imaging operation at each irradiation position 70 in the contrast imaging and the tomosynthesis imaging in this modification example. In the example illustrated in FIG. 7A, information indicating the relationship among the filter used for a first imaging operation, the filter used for a second imaging operation, and the filter used for a third imaging operation at each of the first to seventh irradiation positions $70_1$ to $70_7$ is illustrated. As illustrated in FIG. 7A, at the first irradiation position $70_1$ which is the start position of the tomosynthesis imaging, in the first imaging operation, an imaging process (hereinafter, referred to as a "first imaging process") that emits the radiation R with the first energy (LE) using the first filter to capture a low-energy image is performed. In addition, in the second imaging operation, an imaging process (hereinafter, referred to as a "third imaging process") that emits the radiation R with the third energy (ME) using the third filter to capture a medium-energy image is performed. Therefore, the switching control unit 60 performs control to switch the filter inserted into the irradiation field from the first filter to the third filter between the first imaging operation and the second imaging operation. Further, at the first irradiation position $70_1$, in the third imaging operation, an imaging process (hereinafter, referred to as a "second imaging process") that emits the radiation R with the second energy (HE) using the second filter to capture a high-energy image is performed. Therefore, the switching control unit 60 performs control to switch the filter inserted into the irradiation field from the third filter to the second filter between the second imaging operation and the third imaging operation.

At the next second irradiation position $70_2$, the second imaging process is performed in the first imaging operation. In addition, the third imaging process is performed in the second imaging operation. Therefore, the switching control unit 60 performs control to switch the filter inserted into the irradiation field from the second filter to the third filter between the first imaging operation and the second imaging operation. Further, at the second irradiation position $70_2$, the first imaging process is performed in the third imaging operation. Therefore, the switching control unit 60 performs control to switch the filter inserted into the irradiation field from the third filter to the first filter between the second imaging operation and the third imaging operation.

Further, at the next third irradiation position $70_3$, the first imaging process is performed in the first imaging operation. In addition, the third imaging process is performed in the second imaging operation. Therefore, the switching control unit 60 performs control to switch the filter inserted into the irradiation field from the first filter to the third filter between the first imaging operation and the second imaging operation. Further, at the third irradiation position $70_3$, the second imaging process is performed in the third imaging operation. Therefore, the switching control unit 60 performs control to switch the filter inserted into the irradiation field from the third filter to the second filter between the second imaging operation and the third imaging operation.

Furthermore, FIG. 7B illustrates another example of the filter used for each imaging operation at each irradiation position 70 in the contrast imaging and the tomosynthesis imaging in this modification example. In the example illustrated in FIG. 7B, the order in which the first to third imaging processes are performed at each irradiation position 70 is different from that in the example illustrated in FIG. 7A.

As illustrated in FIG. 7B, at the first irradiation position $70_1$ which is the start position of the tomosynthesis imaging, the first imaging process is performed in the first imaging operation. In addition, the third imaging process is performed in the second imaging operation. Therefore, the switching control unit 60 performs control to switch the filter inserted into the irradiation field from the first filter to the third filter between the first imaging operation and the second imaging operation. Further, at the first irradiation position $70_1$, the second imaging process is performed in the third imaging operation. Therefore, the switching control unit 60 performs control to switch the filter inserted into the irradiation field from the third filter to the second filter between the second imaging operation and the third imaging operation.

At the next second irradiation position $70_2$, the second imaging process is performed in the first imaging operation. In addition, the first imaging process is performed in the second imaging operation. Therefore, the switching control unit 60 performs control to switch the filter inserted into the irradiation field from the second filter to the first filter between the first imaging operation and the second imaging operation. Further, at the second irradiation position $70_2$, the third imaging process is performed in the third imaging operation. Therefore, the switching control unit 60 performs control to switch the filter inserted into the irradiation field from the first filter to the third filter between the second imaging operation and the third imaging operation.

Further, at the next third irradiation position $70_3$, the third imaging process is performed in the first imaging operation. In addition, the second imaging process is performed in the second imaging operation. Therefore, the switching control unit 60 performs control to switch the filter inserted into the irradiation field from the third filter to the second filter between the first imaging operation and the second imaging operation. Further, at the third irradiation position $70_3$, the first imaging process is performed in the third imaging operation. Therefore, the switching control unit 60 performs control to switch the filter inserted into the irradiation field from the second filter to the first filter between the second imaging operation and the third imaging operation.

Further, FIG. 7C illustrates still another example of the filter used for each imaging operation at each irradiation position 70 in the contrast imaging and the tomosynthesis imaging in this modification example. In the example illustrated in FIG. 7C, the order in which the first to third imaging processes are performed at each irradiation position 70 is different from that in the examples illustrated in FIGS. 7A and 7B.

As illustrated in FIG. 7C, at the first irradiation position $70_1$ which is the start position of the tomosynthesis imaging, the third imaging process is performed in the first imaging operation. In addition, the first imaging process is performed in the second imaging operation. Therefore, the switching control unit 60 performs control to switch the filter inserted into the irradiation field from the third filter to the first filter between the first imaging operation and the second imaging operation. Further, at the first irradiation position $70_1$, the second imaging process is performed in the third imaging operation. Therefore, the switching control unit 60 performs control to switch the filter inserted into the irradiation field from the first filter to the second filter between the second imaging operation and the third imaging operation.

At the next second irradiation position $70_2$, the second imaging process is performed in the first imaging operation. In addition, the first imaging process is performed in the second imaging operation. Therefore, the switching control unit 60 performs control to switch the filter inserted into the irradiation field from the second filter to the first filter between the first imaging operation and the second imaging operation. Further, at the second irradiation position $70_2$, the third imaging process is performed in the third imaging operation. Therefore, the switching control unit 60 performs control to switch the filter inserted into the irradiation field from the first filter to the third filter between the second imaging operation and the third imaging operation.

Further, at the next third irradiation position $70_3$, the third imaging process is performed in the first imaging operation. In addition, the first imaging process is performed in the second imaging operation. Therefore, the switching control unit 60 performs control to switch the filter inserted into the irradiation field from the third filter to the first filter between the first imaging operation and the second imaging operation. Further, at the third irradiation position $70_3$, the second imaging process is performed in the third imaging operation. Therefore, the switching control unit 60 performs control to switch the filter inserted into the irradiation field from the first filter to the second filter between the second imaging operation and the third imaging operation.

As described above, in this modification example, the switching control unit 60 that performs the control according to the examples illustrated in FIGS. 7A to 7C performs control to set the filter used for the third imaging operation at the n-th irradiation position 70 to the filter used for the first imaging operation at the (n+1)-th irradiation position 70. Therefore, even in this modification example, the switching control unit 60 does not switch the filter in a case in which the irradiation position 70 is changed. Therefore, similarly to the above-described embodiment, according to the console 12 of this modification example, in the contrast imaging and the tomosynthesis imaging, it is possible to reduce the number of times the filter is switched in the entire tomosynthesis imaging.

In addition, the irradiation control process performed in the mammography apparatus 10 according to this modification example may be a process obtained by modifying the irradiation control process (see FIG. 6) according to the above-described embodiment to a process corresponding to the energy of the radiation R emitted at each irradiation position 70 in each imaging operation. Specifically, a process of sequentially emitting the radiation R with desired energy according to three imaging operations at the first irradiation position $70_1$ between Step S102 and Step S108 of the irradiation control process illustrated in FIG. 6 is performed. Further, a process of sequentially emitting the radiation R with desired energy according to three imaging operations at each irradiation position 70 between Step S108 and Step S114 is performed.

Figure 8:
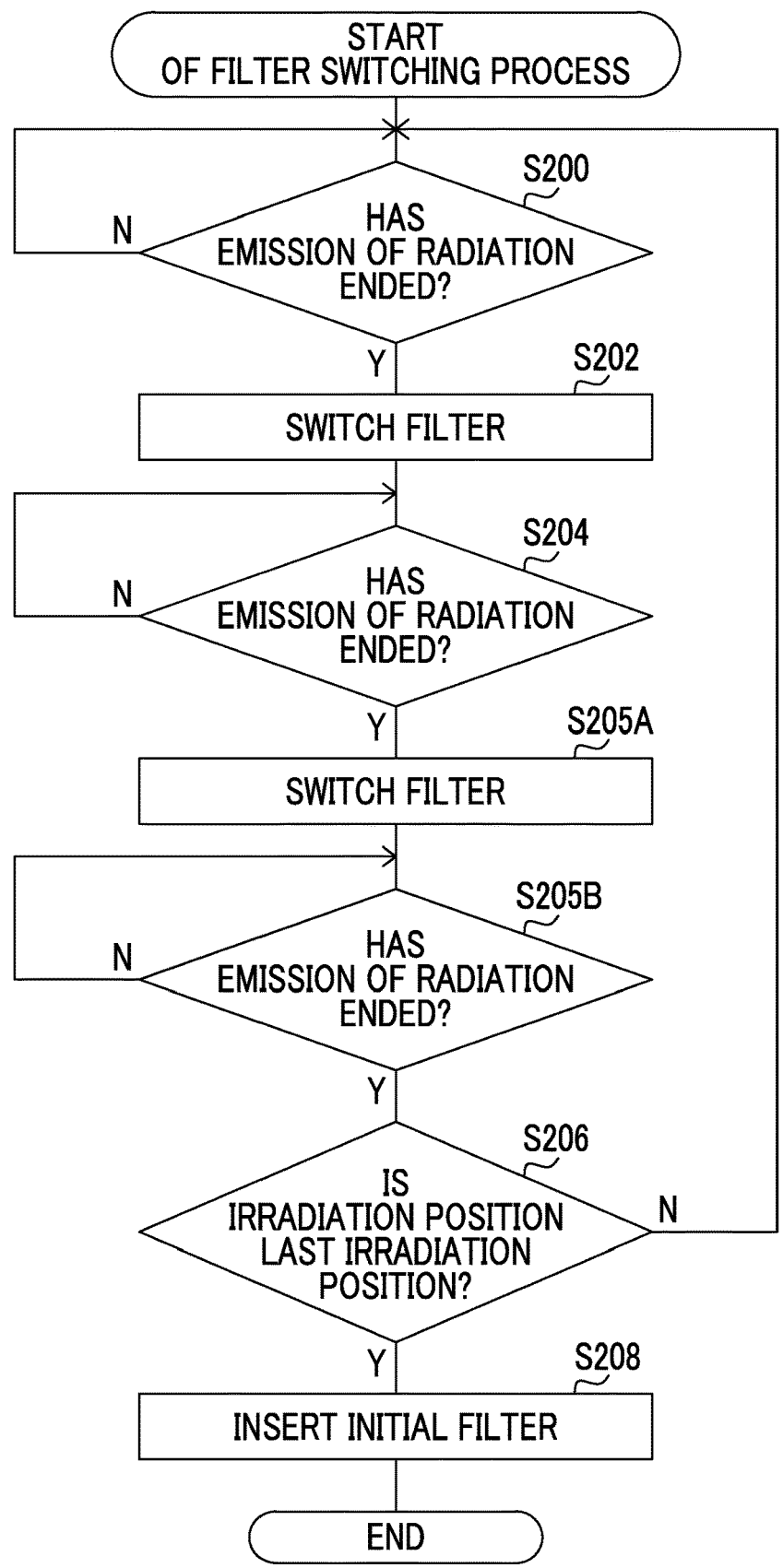
FIG. 8 is a flowchart illustrating an example of the flow of a filter switching process by the console according to the modification example.

On the other hand, the filter switching process performed in the console 12 according to this modification example may be a process obtained by modifying the filter switching process (see FIG. 6) according to the above-described embodiment to a process corresponding to the filter used according to the energy of the radiation R emitted at each irradiation position 70 in each imaging operation. FIG. 8 is a flowchart illustrating an example of the flow of the filter switching process performed in the console 12 according to this modification example. The filter switching process illustrated in FIG. 8 is different from the filter switching process illustrated in FIG. 6 in that processes in Steps S205A and S205B are included between Steps S204 and S206.

In this modification example, as illustrated in FIG. 8, in Step S205A, the switching control unit 60 performs control to switch the filter used for imaging. In other words, the switching control unit 60 performs control to switch the filter inserted into the irradiation field from the filter used for the second imaging operation to the filter used for the third imaging operation.

Then, in Step S205B, the switching control unit 60 determines whether or not the emission of the radiation R has ended in the mammography apparatus 10. In other words, the switching control unit 60 determines whether or not the emission of the radiation R in the third imaging operation has ended. The determination result in Step S205B is "No" until the emission of the radiation R ends. On the other hand, in a case in which the emission of the radiation R ends, the determination result in Step S205B is "Yes", and the process proceeds to Step S206.

As described above, in the filter switching process according to this modification example, a process of switching the filter used for imaging between the second imaging operation and the third imaging operation at each irradiation position 70 is performed. In other words, the switching of the filter and the determination of whether or not to end the emission of the radiation R are performed the number of times obtained by subtracting 1 from the number of imaging operations at each irradiation position 70, specifically, the number of imaging operations performed at each irradiation position 70 while changing the filter used. Therefore, in this modification example, it is possible to appropriately switch the filter used for imaging as in the above-described embodiment.

In addition, in a case in which three or more radiographic images are captured at each irradiation position 70 as described above, the image processing device may generate a plurality of types of difference tomographic images. For example, according to this modification example, the image processing device can generate three types of difference tomographic images, that is, a difference tomographic image corresponding to the difference between the medium-energy image and the low-energy image, a difference tomographic image corresponding to the difference between the high-energy image and the medium-energy image, and a difference tomographic image corresponding to the difference between the high-energy image and the low-energy image. Therefore, the image processing device may generate two or more of the three types of difference tomographic images.

As described above, the console 12 according to the above-described embodiment comprises the CPU 50A as at least one processor. The CPU 50A performs control to set the last filter used at the n-th irradiation position 70 as the initial filter used at the (n+1)-th irradiation position 70 in the tomosynthesis imaging which uses the radiation source 29 that generates the radiation R and the Al filter 30 and the Cu filter 32 that change the quality of the radiation R, irradiates the breast with the radiation R emitted from the radiation source 29 at a plurality of irradiation positions 70 having different irradiation angles, and switches the Al filter 30 and the Cu filter 32 at each irradiation position 70 such that the radiation R having different qualities is emitted to capture a plurality of radiographic images of the breast at each irradiation position.

As described above, the console 12 according to the above-described embodiment performs control to set the filter used for the last imaging operation at the n-th irradiation position 70 as the filter used for the initial imaging operation at the (n+1)-th irradiation position 70. Therefore, the console 12 according to the above-described embodiment does not switch the filter in a case in which the irradiation position 70 is moved. For example, in some cases, the types of the filters used for the initial imaging operation at each irradiation position 70 are the same, and the type of the filter used for the last imaging operation at each irradiation position 70 is different from the type of the filter used for the initial imaging operation at the next irradiation position 70. In this case, it is necessary to switch the filter used in a case in which the irradiation position 70 is moved. Therefore, in some cases, it is necessary to switch the filter whenever imaging is performed. On the other hand, in the above-described embodiment, the filter may not be switched in a case in which the irradiation position 70 is moved. Therefore, according to the console 12 of the above-described embodiment, in the tomosynthesis imaging in which images are captured a plurality of times at each of the plurality of irradiation positions 70, it is possible to reduce the number of times the filter is switched in the entire tomosynthesis imaging.

Further, in the above-described embodiment, the aspect in which the console 12 is an example of the imaging control device according to the present disclosure has been described. However, devices other than the console 12 may have the functions of the imaging control device according to the present disclosure. In other words, for example, the mammography apparatus 10 or an external device other than the console 12 may have some or all of the functions of the switching control unit 60.

Figure 9:
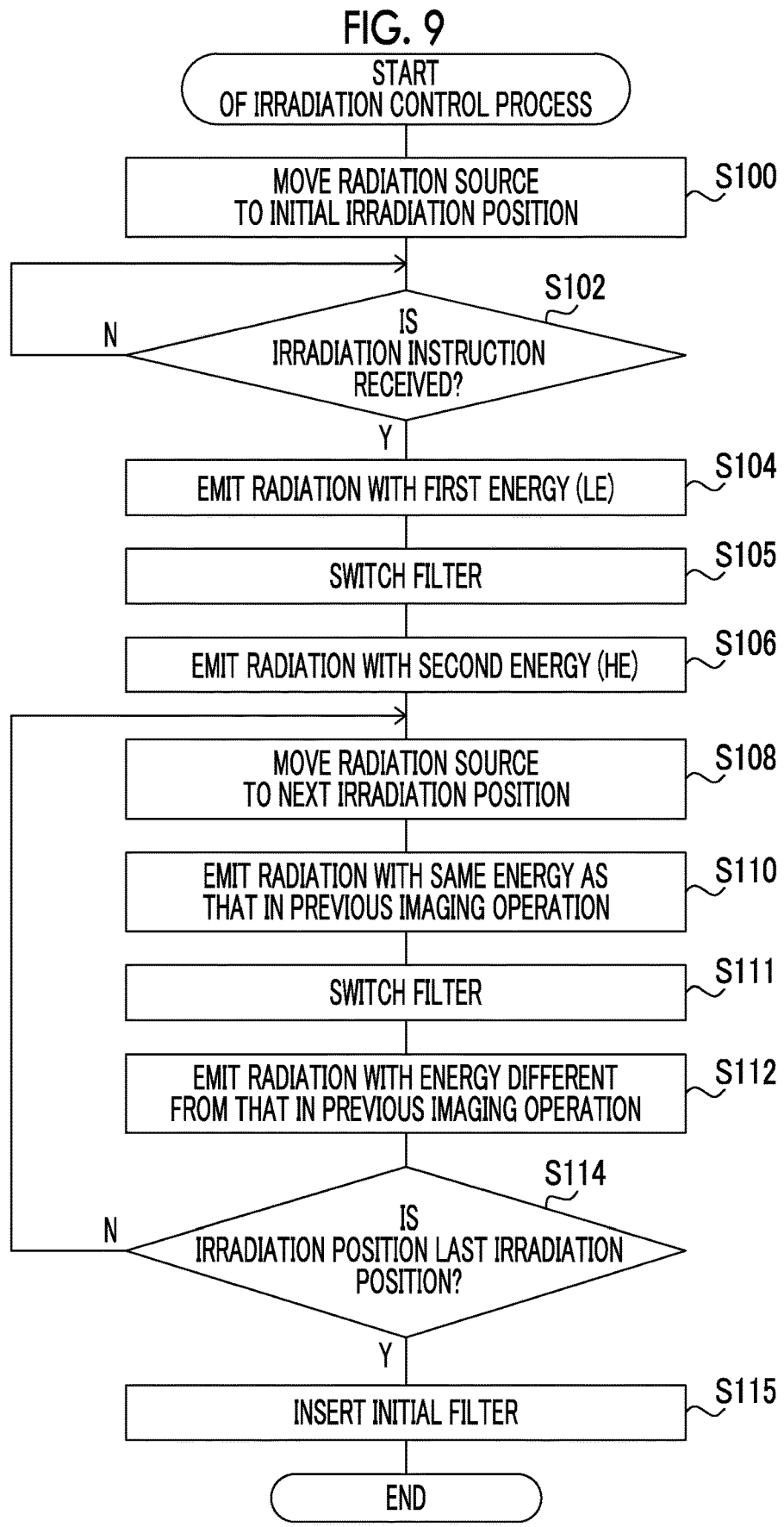
FIG. 9 is a flowchart illustrating another example of the flow of the irradiation control process by the mammography apparatus according to the embodiment.

As a specific example, an aspect in which the mammography apparatus 10 has the functions of the imaging control device according to the present disclosure will be described. In this case, for example, the control unit 40 of the mammography apparatus 10 may function as the switching control unit 60. Specifically, the irradiation control program 41 executed by the CPU 40A of the control unit 40 in the mammography apparatus 10 may be a program obtained by combining the irradiation control program 41 and the switching control program 51 according to the above-described embodiment. In this case, the irradiation control program 41 corresponds to an example of an imaging control unit according to the present disclosure. FIG. 9 is a flowchart illustrating an example of the flow of the irradiation control process by the mammography apparatus in this case.

The irradiation control process illustrated in FIG. 9 differs from the irradiation control process illustrated in FIG. 6 in that it includes a process in Step S105 between Steps S104 and S106, a process in Step S111 between Steps S110 and S112, and a process in Step S115 after Step S114.

In the process in Step S105 illustrated in FIG. 9, the switching control unit 60 switches the filter used for imaging from the Al filter 30 used for imaging in Step S104 to the Cu filter 32 used for imaging in Step S106. In addition, in the process in Step S111, the switching control unit 60 switches the filter used for imaging from the filter used for imaging in Step S110 to the filter used for imaging in Step S112. Further, in the process in Step S115, the switching control unit 60 performs control such that the initial filter is inserted into the irradiation field as in Step S208 of the filter switching process illustrated in FIG. 6.

As described above, according to the irradiation control process illustrated in FIG. 9, the mammography apparatus 10 can perform control to set the filter used for the last imaging operation at the n-th irradiation position 70 as the filter used for the initial imaging operation at the (n+1)-th irradiation position 70.

In addition, in the above-described embodiment, the aspect in which the breast is applied as an example of the object according to the present disclosure and the mammography apparatus 10 is applied as an example of the radiography apparatus according to the present disclosure has been described. However, the object is not limited to the breast, and the radiography apparatus is not limited to the mammography apparatus. For example, the object may be the chest, the abdomen, or the like, and radiography apparatuses other than the mammography apparatus may be applied.

Further, in the above-described embodiment, the aspect in which the contrast imaging and the tomosynthesis imaging are as an example of the tomosynthesis imaging according to the present disclosure has been described. However, the present disclosure is not limited to this aspect. For example, so-called energy subtraction imaging may be performed. In addition to the contrast imaging, an aspect in which a high-energy image in which a bone portion has been highlighted and a low-energy image in which a soft portion has been highlighted are captured is given an example of the energy subtraction imaging. In this case, a difference image indicating the difference between the high-energy image and the low-energy image can be generated to perform, for example, the observation of the bone portion or the soft portion of the object and the derivation of bone mineral density.

Furthermore, in the above-described embodiment, for example, the following various processors can be used as the hardware structure of processing units performing various processes such as the control unit 40, the control unit 50, and the switching control unit 60. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the irradiation control program 41 is stored (installed) in the ROM 40B in advance and the switching control program 51 is stored (installed) in the ROM 50B in advance has been described. However, the present disclosure is not limited thereto. Each of the irradiation control program 41 and the switching control program 51 may be recorded on a recording medium, such as a compact disc read only memory (CD-ROM), a digital versatile disc read only memory (DVD-ROM), or a universal serial bus (USB) memory, and then provided. Furthermore, each of the irradiation control program 41 and the switching control program 51 may be downloaded from an external device through the network.

Moreover, instead of the switching control unit 60 using the processor, a filter switching mechanism without the processor may be applied. For example, in a case in which the filter used for imaging is predetermined according to the irradiation position 70, the number of imaging operations, or the like as described above, the radiography system 1 may be configured to comprise a filter switching mechanism having a mechanical mechanism that appropriately inserts the filter into the irradiation field as determined in advance.

Figure 10:
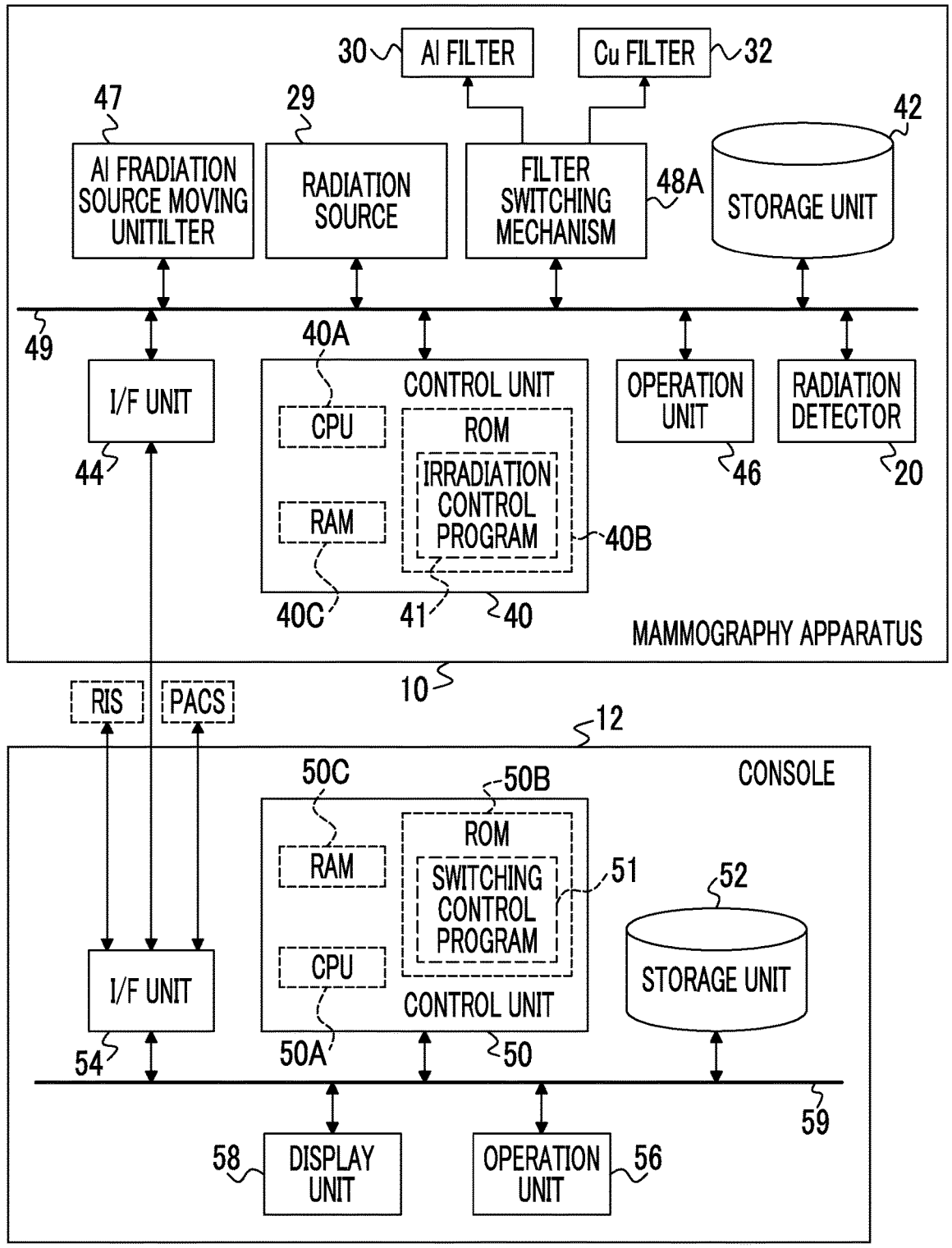
FIG. 10 is a block diagram illustrating another example of the configuration of the mammography apparatus and the console according to the embodiment.

FIG. 10 is a block diagram illustrating an example of the configuration of a mammography apparatus 10 and a console 12 according to this aspect. A filter switching mechanism 48A illustrated in FIG. 10 has a function of switching the filter using a mechanical mechanism according to, for example, the start timing of imaging and the emission timing of radiation, in addition to the functions of the filter switching unit 48 in the mammography apparatus 10.

That is, the radiography system 1 may comprise: a radiation source 29 that generates the radiation R; a plurality of types of filters that change the energy of the radiation R generated by the radiation source 29; and a filter switching mechanism that, in a case in which a radiography apparatus irradiates an object with the radiation R emitted from the radiation source 29 at a plurality of irradiation positions 70 having different irradiation angles and captures a plurality of radiographic images of the object obtained by the irradiation with the radiation R having different energy levels at each irradiation position 70, switches the plurality of types of filters at each irradiation position 70 and switches the last filter used at the n-th irradiation position 70 to the initial filter used at the (n+1)-th irradiation position 70.

What is claimed is:

1. An imaging control device comprising:
at least one processor,
wherein, in tomosynthesis imaging which uses a radiation source that generates radiation and a plurality of types of filters that change a quality of the radiation, irradiates an object with the radiation emitted from the radiation source at a plurality of irradiation positions having different irradiation angles, and switches the plurality of types of filters at each of the irradiation positions such that the radiation having different qualities is emitted to capture a plurality of radiographic images of the object at each of the irradiation positions, the processor performs control to set a last filter used at an n-th irradiation position as an initial filter used at an (n+1)-th irradiation position.

2. The imaging control device according to claim 1, wherein the plurality of types of filters include a first filter that is used in a case in which radiation with first energy is emitted and a second filter that is used in a case in which radiation with second energy higher than the first energy is emitted, and
the processor performs control to use the first filter as the initial filter at an initial irradiation position among the plurality of irradiation positions.

3. The imaging control device according to claim 1, wherein the plurality of types of filters are three or more filters that are used in a case in which radiation with different energy levels is emitted, and
the processor performs control to set a filter that is used in a case in which radiation with the lowest energy is emitted as the initial filter at an initial irradiation position among the plurality of irradiation positions.

4. A radiography system comprising:
a radiography apparatus that includes a radiation source which generates radiation and a plurality of types of filters which change energy of the radiation generated by the radiation source, irradiates an object with the radiation emitted from the radiation source at a plurality of irradiation positions having different irradiation angles, and switches the plurality of types of filters at each of the irradiation positions such that the radiation having different energy levels is emitted to capture a plurality of radiographic images of the object at each of the irradiation positions; and the imaging control device according to claim 1.

5. A radiography system comprising:

a radiation source that generates radiation;

a plurality of types of filters that change energy of the radiation generated by the radiation source; and a filter switching mechanism that, in a case in which a radiography apparatus irradiates an object with the radiation emitted from the radiation source at a plurality of irradiation positions having different irradiation angles and captures a plurality of radiographic images of the object obtained by the irradiation with the radiation having different energy levels at each of the irradiation positions, switches the plurality of types of filters at each of the irradiation positions and switches a last filter used at an n-th irradiation position to an initial filter used at an (n+1)-th irradiation position.

6. An imaging control method executed by a computer, the imaging control method comprising:

in tomosynthesis imaging which uses a radiation source that generates radiation and a plurality of types of filters that change a quality of the radiation, irradiates an object with the radiation emitted from the radiation source at a plurality of irradiation positions having different irradiation angles, and switches the plurality of types of filters at each of the irradiation positions such that the radiation having different qualities is emitted to capture a plurality of radiographic images of the object at each of the irradiation positions, performing control to set a last filter used at an n-th irradiation position as an initial filter used at an (n+1)-th irradiation position.

7. A non-transitory computer-readable storage medium storing an imaging control program that causes a computer to perform a process of:

in tomosynthesis imaging which uses a radiation source that generates radiation and a plurality of types of filters that change a quality of the radiation, irradiates an object with the radiation emitted from the radiation source at a plurality of irradiation positions having different irradiation angles, and switches the plurality of types of filters at each of the irradiation positions such that the radiation having different qualities is emitted to capture a plurality of radiographic images of the object at each of the irradiation positions, performing control to set a last filter used at an n-th irradiation position as an initial filter used at an (n+1)-th irradiation position.

* * * * *